(12) United States Patent
Chang et al.

(10) Patent No.: US 10,280,456 B2
(45) Date of Patent: *May 7, 2019

(54) OPTICAL DETECTION FOR BIO-ENTITIES

(71) Applicant: Taiwan Semiconductor Manufacturing Company, Ltd., Hsin-Chu (TW)

(72) Inventors: Allen Timothy Chang, Hsinchu (TW); Yi-Hsien Chang, Changhua County (TW); Chun-Ren Cheng, Hsin-Chu (TW)

(73) Assignee: TAIWAN SEMICONDUCTOR MANUFACTURING COMPANY, LTD., Hsin-Chu (TW)

( * ) Notice: Subject to any disclaimer, the term of this patent is extended or adjusted under 35 U.S.C. 154(b) by 399 days.

This patent is subject to a terminal disclaimer.

(21) Appl. No.: 15/179,637

(22) Filed: Jun. 10, 2016

(65) Prior Publication Data

US 2016/0281158 A1  Sep. 29, 2016

Related U.S. Application Data

(63) Continuation of application No. 13/830,234, filed on Mar. 14, 2013, now Pat. No. 9,366,647.

(51) Int. Cl.
*G01N 27/447* (2006.01)
*C12Q 1/6869* (2018.01)
(Continued)

(52) U.S. Cl.
CPC ........ *C12Q 1/6869* (2013.01); *B01F 13/0071* (2013.01); *B01F 13/0076* (2013.01);
(Continued)

(58) Field of Classification Search
CPC . B01L 3/502784–3/502792; B01L 2200/0673; B01L 2200/0654; B01L 2400/0424; B01L 2400/0427; F15C 3/002
See application file for complete search history.

(56) References Cited

U.S. PATENT DOCUMENTS

| | | |
|---|---|---|
| 8,791,557 B2 | 7/2014 | Chang |
| 9,239,328 B2 | 1/2016 | Chang |
| | (Continued) | |

OTHER PUBLICATIONS

Mark A Burns et al., "An Integrated Nanoliter DNA Analysis Device," Science, published by American Association for the Advancement of Science, Oct. 16, 1998, vol. 282, pp. 484-487.
(Continued)

*Primary Examiner* — J. Christopher Ball
(74) *Attorney, Agent, or Firm* — Haynes and Boone, LLP

(57) ABSTRACT

An integrated semiconductor device for manipulating and processing bio-entity samples and methods are described. The device includes a lower substrate, at least one optical signal conduit disposed on the lower substrate, at least one cap bonding pad disposed on the lower substrate, a cap configured to form a capped area, and disposed on the at least one cap bonding pad, a fluidic channel, wherein a first side of the fluidic channel is formed on the lower substrate and a second side of the fluidic channel is formed on the cap, a photosensor array coupled to sensor control circuitry, and logic circuitry coupled to the fluidic control circuitry, and the sensor control circuitry.

20 Claims, 15 Drawing Sheets

(51) Int. Cl.
  *G01N 21/05* (2006.01)
  *G01N 21/64* (2006.01)
  *B01L 3/00* (2006.01)
  *B01F 13/00* (2006.01)
  *G02B 6/122* (2006.01)
  *G01N 21/03* (2006.01)

(52) U.S. Cl.
  CPC ... *B01L 3/502707* (2013.01); *B01L 3/502792* (2013.01); *G01N 21/05* (2013.01); *G01N 21/6428* (2013.01); *G01N 27/44721* (2013.01); *G01N 27/44791* (2013.01); *B01L 2300/0654* (2013.01); *B01L 2300/089* (2013.01); *B01L 2300/0819* (2013.01); *B01L 2300/0867* (2013.01); *B01L 2300/165* (2013.01); *B01L 2300/168* (2013.01); *B01L 2400/0427* (2013.01); *G01N 2021/0325* (2013.01); *G01N 2021/058* (2013.01); *G01N 2021/6482* (2013.01); *G01N 2201/08* (2013.01); *G02B 6/122* (2013.01)

(56) References Cited

U.S. PATENT DOCUMENTS

| 9,366,647 B2 * | 6/2016 | Chang ............ G01N 27/44721 |
| 2004/0027462 A1 | 2/2004 | Hing |
| 2004/0231990 A1 | 2/2004 | Aubry |
| 2009/0302228 A1 | 12/2009 | Hadjioannou |
| 2011/0118132 A1 | 5/2011 | Winger |

OTHER PUBLICATIONS

Aaron R. Wheeler, "Putting Electrowetting to Work," Science, published by American Association for the Advancement of Science, Oct. 24, 2008, vol. 322, pp. 539-540.

Mohamed Abdelgawad et al., "The Digital Revolution: A New Paradigm for Microfluidics," 2009 Wiley-VCH Verlag GmbH & Co. KGaA Weinheim, pp. 920-925.

* cited by examiner

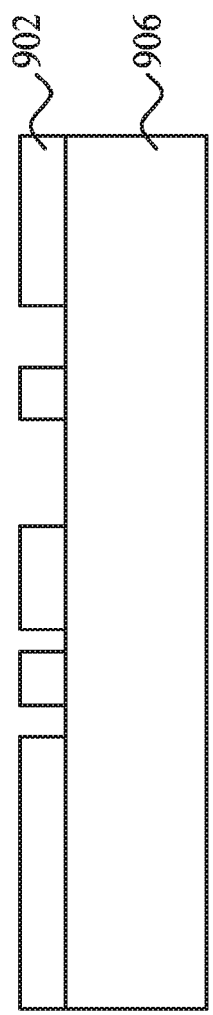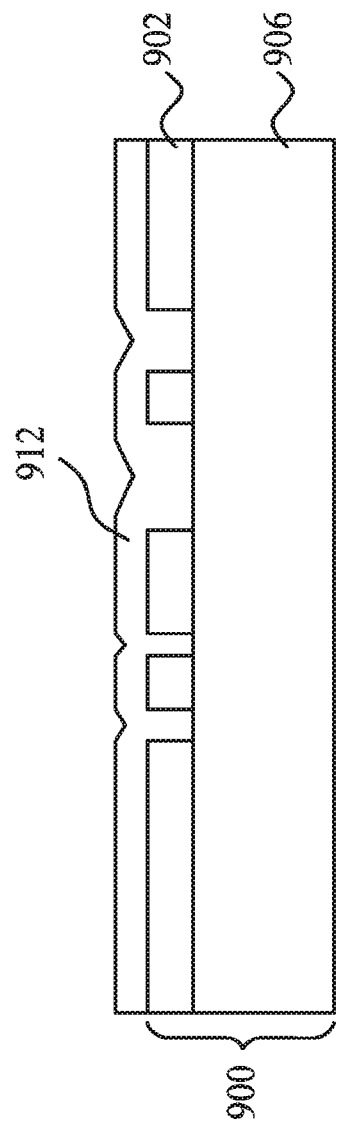

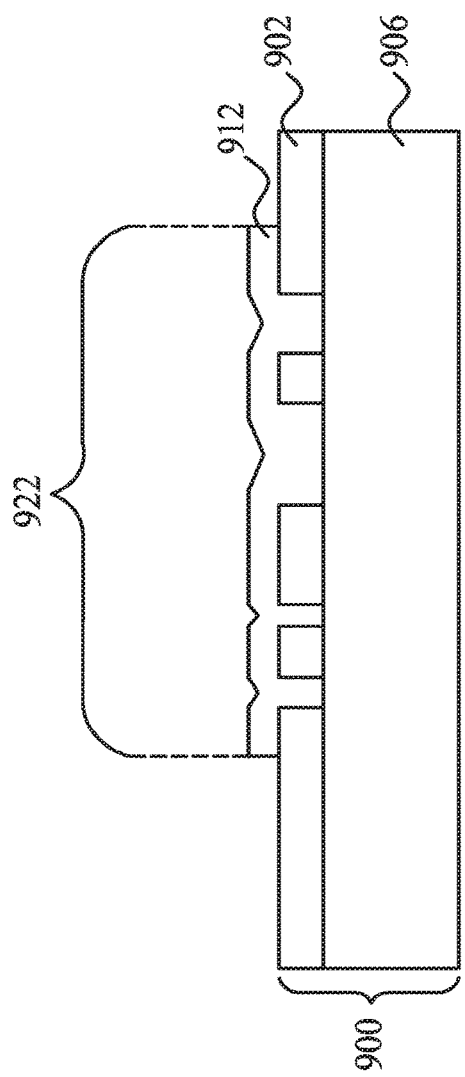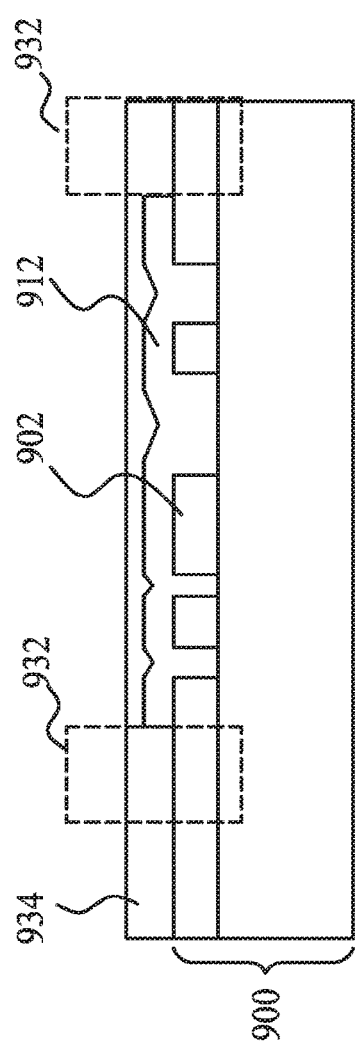

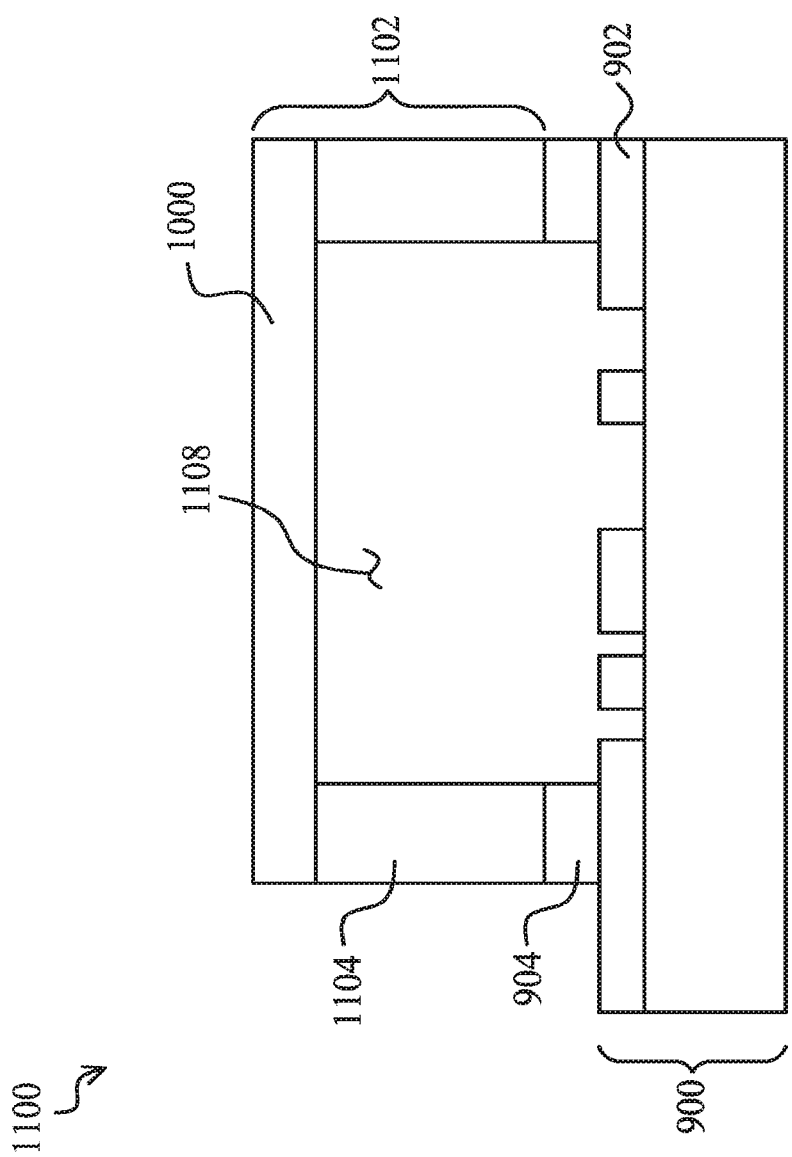

OPTICAL DETECTION FOR BIO-ENTITIES

BACKGROUND

This is a continuation of U.S. Ser. No. 13/830,234 filed Mar. 14, 2013, the entirety of which is hereby incorporated by reference.

Medical technology industries, including device manufactures as well as pharmaceuticals and biologics manufacturers, have experienced significant commercial and technological growth over the past several decades. Since the discovery of DNA, our understanding of its bio-informational role in the development, operation, and interaction of all living beings has significantly increased thanks to the development of DNA sequencing techniques over the years. Through improvement in DNA sequencing detection techniques, scientists and doctors have gained greater insight on diseases as well as more effective treatments for patients based on their genetic dispositions. Thus, the use and role of DNA sequencing results in health care has increased significantly.

DNA sequences are series of the nucleotide bases adenine, guanine, cytosine, and thymine, that dictate the formation of proteins in biological systems. By analyzing a DNA sequence, important information can be gleaned for both diagnostic and therapeutic purposes. Additionally, the identification and quantification of other biological entities (bio-entities), such as proteins, small molecules, and pathogens has pushed forward the potential of medical knowledge to benefit humankind.

Packaged sequencers employing electrowetting-on-dielectric (EWOD) for control use amplification and labeling techniques that allow for optical detection by using fluorescent dyes and external optical systems with analog-to-digital conversion systems to allow for the computer processing required for handling the large amounts of data produced. Many implementations of packaged EWOD sequencers have a glass substrate and a transparent electrode, which can be problematic. For example, light can be transmitted through the glass substrate and into the droplet being analyzed, where sequencing is happening. In such case, transmission may not be efficient because of interference patterns from different transparent index of refractions as well as different thicknesses of transparent material. In addition, the integration of color filters into EWOD sequencers can reduce efficiency of light sent into a sensor array.

Therefore, a need exists for improved bio-entity manipulation devices and processing technologies.

BRIEF DESCRIPTION OF DRAWINGS

FIGS. 9A-9F are cross-sectional diagrams illustrating embodiments of a method for forming a lower wafer for use in a bio-entity manipulation and processing system according to an embodiment.

FIGS. 11A and 11B are side view diagrams illustrating embodiments of bonding a lower wafer and an upper wafer for use in a bio-entity manipulation and processing system according to an embodiment.

Figure 1:
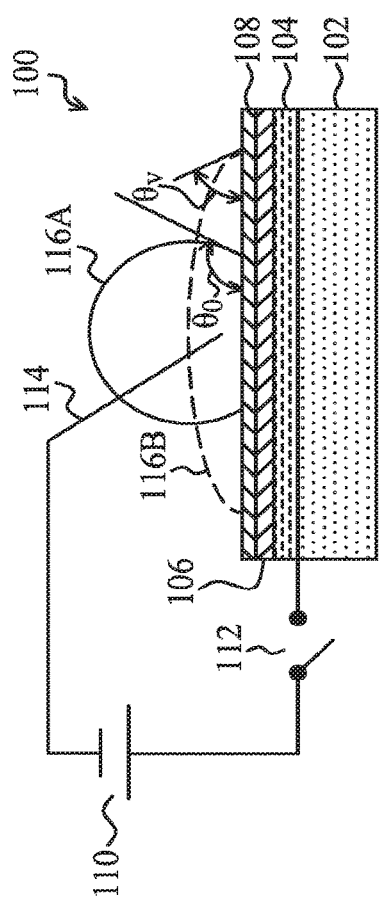
FIG. 1 is a cross-sectional diagram of an EWOD apparatus.

The various features disclosed in the drawings briefly described above will become more apparent to one of skill in the art upon reading the detailed description below.

DETAILED DESCRIPTION

It is to be understood that the following disclosure provides many different embodiments and examples for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features in the figures may be arbitrarily drawn in different scales for the sake of simplicity and clarity. Where features depicted in the various figures are common between two or more figures, the same identifying numerals have been used for clarity of description. However, this should not be understood as limiting such features.

FIG. 1 is a cross-sectional diagram of an electro-wetting-on-dielectric (EWOD) apparatus 100. The apparatus 100 includes a substrate 102 with three material layers thereon. These material layers include an electrode layer 104, a dielectric layer 106, and a hydrophobic coating 108. The electrode layer 104 is coupled to a variable voltage source 110 by a switch 112. Attached to the opposite end of the voltage source 110 is a probe 114. As depicted in FIG. 1, the apparatus 100 positions the probe 114 to be inserted into a droplet shown in two different states. Droplet 116A depicts the droplet in a state when no voltage is being applied by probe 114. Because of the hydrophobic coating 108, droplet 116A has a contact angle $\theta_0$ as shown. By applying a voltage from the voltage source 110 through the probe 114, the contact angle can be decreased and the contact area increased. Thus, droplet 116B is the droplet when a voltage is applied. The contact angle is then decreased to $\theta_v$, bringing the mass of the droplet 116 B closer to the underlying electrode layer 104. The change in the contact angle caused by the applied voltage is related to the applied voltage according to equation (1) below.

$$\cos\theta_V - \cos\theta_0 = \frac{\varepsilon\varepsilon_o}{2\gamma_{LG}t}V^2 \quad (1)$$

In equation (1), V is the applied electrical potential or voltage, $\theta_V$ is the contact angle under applied voltage V, and $\theta_0$ is the contact angle without applied voltage V. Other variables include: $\varepsilon$, the dielectric constant of the dielectric layer 106; $\varepsilon_0$, the vacuum permittivity; $\gamma_{LG}$, the surface tension; and t, the thickness of dielectric layer 106. This manipulation of the apparent hydrophobicity of the droplet in apparatus 100 may be referred to as electrowetting-on-dielectric (EWOD). Thus, by using EWOD, the physical configuration of a droplet on a hydrophobic surface can be altered and controlled as seen in FIG. 1.

Figure 2:
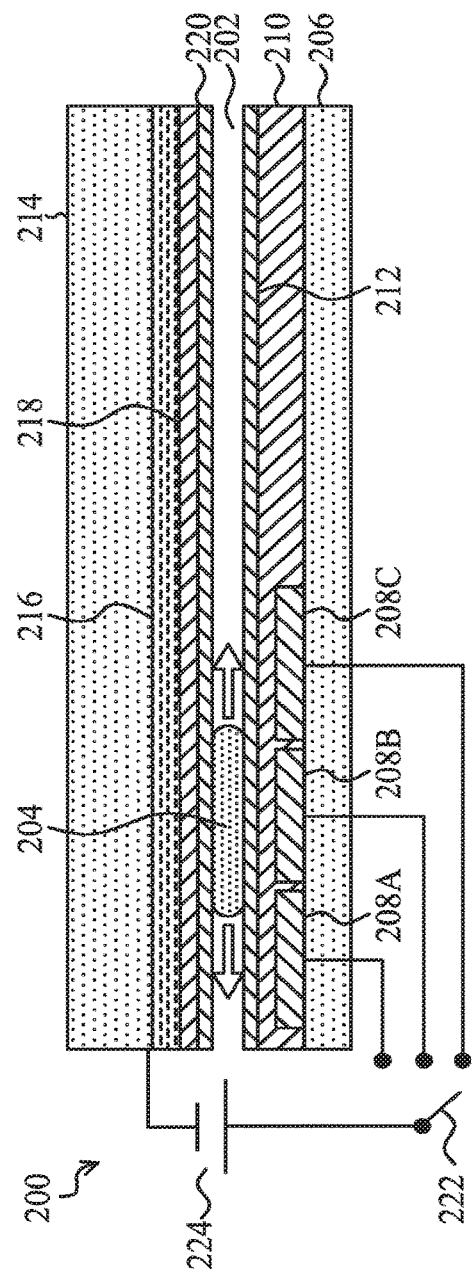
FIG. 2 is a cross-sectional diagram of a fluidic control system that uses electrowetting to transport and manipulate bio-entity sample droplets.

FIG. 2 is a cross-sectional diagram of a fluidic control system 200 that allows for transporting and manipulating bio-entity sample droplets using EWOD principles. The fluidic control system 200 operates around a microfluidic channel 202 to control a droplet 204 within the channel. Droplet 204 is a bio-entity sample droplet. A "bio-entity" or "biological entity" as used herein may refer to DNA, RNA, a protein, a small molecule, a virus or other pathogen, or any such thing that may be sequenced, identified, or quantified. Such activities may take place in a medical or industrial context. Throughout the disclosure, the example of DNA sequencing is presented; however, the embodiments are not limited to this example.

As seen in FIG. 2, the bottom portion of the microfluidic channel 202 is provided by a lower substrate 206 with several layers thereon. These layers include three electrodes 208A, 208B, and 208C, which are surrounded by a first dielectric layer 210. Above the dielectric layer 210 is a first hydrophobic coating 212 that provides the lower surface of the microfluidic channel 202.

The top surface of the microfluidic channel 202 is provided by another hydrophobic coating, which is formed over a upper substrate 214. This upper substrate 214 is a substrate upon which several material layers are deposited. These layers include a top electrode layer 216, a second dielectric layer 218, and a second hydrophobic coating 220, which forms the top surface of the microfluidic channel 202. The upper substrate 214 is inverted and brought close to the surface of the first hydrophobic coating 212. Thus, the droplet 204 is physically bounded by the first hydrophobic coating 212 on the bottom and the second hydrophobic coating 220 on the top.

The bottom electrodes 208A, 208B, and 208C are coupled to a switch 222 capable of selecting any combination of these three electrodes. The switch 222, in turn is connected to a voltage source 224, the opposite side of which is connected to the top electrode layer 216. By selectively applying a voltage to various combinations of electrodes 208A, 208B, and 208C, the electric field in which the droplet 204 is located can be altered. In the depicted embodiment a DC potential is applied, but in other embodiments, an AC potential may be used instead. By controlling the electric fields between the bottom electrodes 208A, 208B, and 208C and the top electrode 216, the droplet 204 itself can be manipulated and transported in various ways. This can be better understood by reference to FIG. 3.

Figure 3:
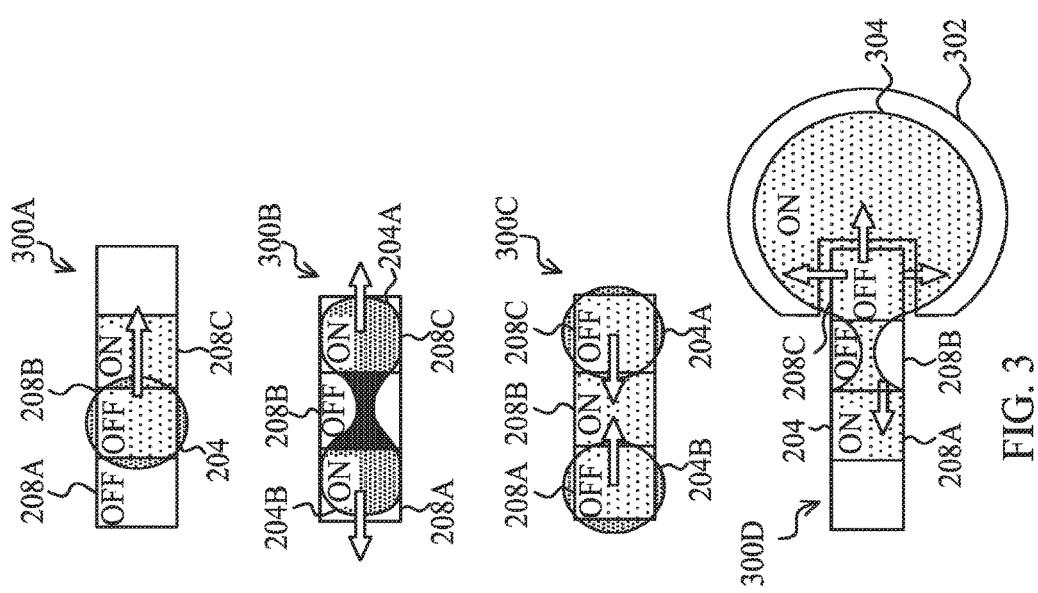
FIG. 3 is a diagram illustrating how certain actions may be achieved using an electrowetting fluidic control system.

FIG. 3 is a diagram illustrating how certain actions may be achieved using an EWOD fluidic control system. Four exemplary actions are depicted: a lateral movement 300A, a droplet split 300B, a droplet merger 300C, and a droplet formation 300D. These examples depict actions performed in the fluidic control system 200 as seen from above, looking down onto the droplet 204 through substrate 214.

As depicted in the lateral movement 300A, the droplet 204 is situated above the electrode 208B. When switch 222 is asserted so that bottom electrode 208A is disconnected from the voltage source 224 (OFF), bottom electrode 208B is OFF, and bottom electrode 208C is connected to the voltage source 224 (ON), the droplet moves in the direction of electrode 208C until it is located over electrode 208C.

As depicted in the droplet split 300B, droplet 204 begins situated above bottom electrode 208B. When switch 222 is asserted so that the bottom electrode 208B is OFF and both bottom electrodes 208A and 208C are ON, the portion of the droplet 204 that is closest to bottom electrode 208A will move to the left and the portion of the droplet 204 that is closest to bottom electrode 208C will move to the right, causing the droplet 204 to be split into a droplet 204A situated over the bottom electrode 208C and a droplet 204B situated over the bottom electrode 208A.

As depicted in the droplet merger 300C, the droplet 204A begins situated above 208C and the droplet 204B begins situated over 208A. When the switch 222 is asserted so that bottom electrodes 208A and 208C are OFF and the bottom electrode 208B is ON, the droplets 204A and 204B both move toward the bottom electrode 208B. The droplets 204A and 204B will merge over the bottom electrode 208B to form a single droplet.

A droplet formation 300D is also depicted in FIG. 3. Droplet formation 300D depicts the formation of a bio-entity sample droplet from a larger bio-entity sample drop. The performance of droplet formation 300D uses the three bottom electrodes 208A, 208B, and 208C, as discussed, and further includes a larger electrode 302. The larger electrode 302 may allow for the placement of a larger volume of liquid in a drop 304. In order to form a droplet 204, all four electrodes (302, 208A, 208B, and 208C) are turned ON to pull the drop 304 out along the path indicated by the square bottom electrodes, then bottom electrodes 208B and 208C are turned OFF. The liquid over bottom electrodes 208B and 208C is pulled away by the ON state of the other electrodes, and pushed away by the hydrophobicity of the bottom electrodes 208B and 208C in their OFF state. The portion of drop 304 above 208A remains to form droplet 204.

These examples assume that any other adjacent electrodes are OFF. The lateral movement 300A, the droplet split 300B, the droplet merger 300C, and the droplet formation 300D actions may be used to manipulate and transport droplets as they move through the microfluidic channel 202 of FIG. 2, and also through a microfluidic grid.

Figure 4:
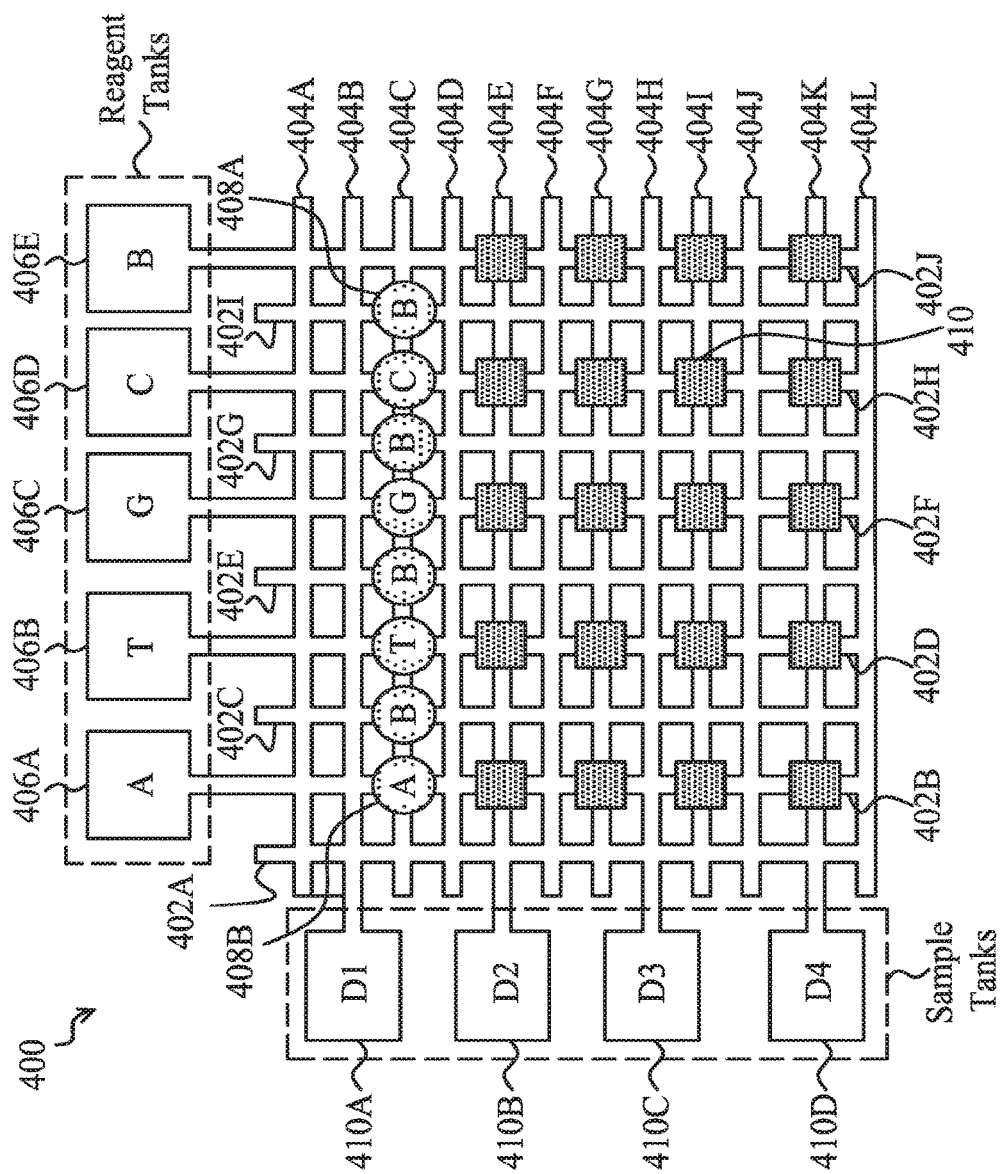
FIG. 4 is a diagram of a microfluidic grid for transporting and mixing target bio-entity samples and biological reagents.

FIG. 4 is a diagram of a microfluidic grid 400 for transporting and mixing target bio-entities or molecules. For example microfluidic grid 400 may be used for transporting and mixing target DNA samples and biological reagents. The microfluidic grid includes a plurality of horizontal and vertical paths lined by electrodes like the electrodes 208A, 208B, and 208C of FIG. 2. Actions like those described in connection with FIG. 3 may be used to move, split, merge, and form droplets in the microfluidic grid 400.

The plurality of vertical paths is labeled as vertical paths 402 A-J, while the plurality of horizontal paths is labeled as horizontal paths 404A-L. Each of vertical paths 402A-J and each of horizontal paths 404A-L may be formed from a plurality of linearly arranged electrodes. The spaces in between the vertical paths 402A-J and the horizontal paths 404A-L may be empty space as the hydrophobic coatings 212 and 220 may effectively bar a droplet from "jumping" from one hydrophilic path to another with electrodes in an ON state. In some embodiments, material barriers exist in the spaces between the paths.

The microfluidic grid 400 also includes a plurality of tanks from which droplets are introduced into the plurality of paths. Arranged along the top are a number of reagent tanks 406A-E. In the depicted embodiment of microfluidic grid 400, these reagent tanks include an adenine reagent tank 406A, a thymine reagent tank 406B, a guanine reagent tank 406C, a cytosine reagent tank 406D, and a buffer tank 406E. Other embodiments of microfluidic grid 400 may include other biological reagents. Droplets may be dispensed into the microfluidic grid 400 through vertical paths 402B, 402D, 402F, 402H, and 402J, and by selectively asserting the electrodes that make up the horizontal and vertical paths, these droplets may be positioned any where in the microfluidic grid 400 and divided and mixed, or merged, with other droplets. A number of reagent droplets, including exemplary buffer droplet 408A and exemplary adenine reagent droplet 408B, are depicted along horizontal path 404C.

Depicted on the left-hand side of microfluidic grid 400 is a number of bio-entity sample tanks 410A-D. In the depicted embodiment, used for DNA sequences, each bio-entity sample tank contains a different target DNA fragment, labeled as D1 in target DNA fragment tank 410A, D2 in target DNA fragment tank 410B, D3 in target DNA fragment tank 410C, and D4 in target DNA fragment tank 410D. In embodiments used for DNA sequencing these tanks hold fragments of a DNA sample to be sequenced. In embodiments used for diagnosis, other types of bio-entity samples, such as antibodies, may be present in the sample tanks.

Sequencing the entire genome of a person or pathogen in a single sequence would require a prohibitively long amount of time. By fragmenting a DNA sample into many samples, each sample may be processed simultaneously in order to decrease the total time required to obtain the entire sequence. The fragments should be labeled beforehand so that the individual parallel sequencing can be recombined. Each square in FIG. 4 is a target DNA fragment, such as exemplary target DNA fragment 410, that can be manipulated as described above in connection with FIG. 3, including being mixed with a reagent droplet for tagging. The area underneath the microfluidic grid 400 includes a light sensor array, which may be used to take light-based measurements in order to sequence the target DNA fragment samples. This may be better understood with reference to FIG. 5.

Figure 5:
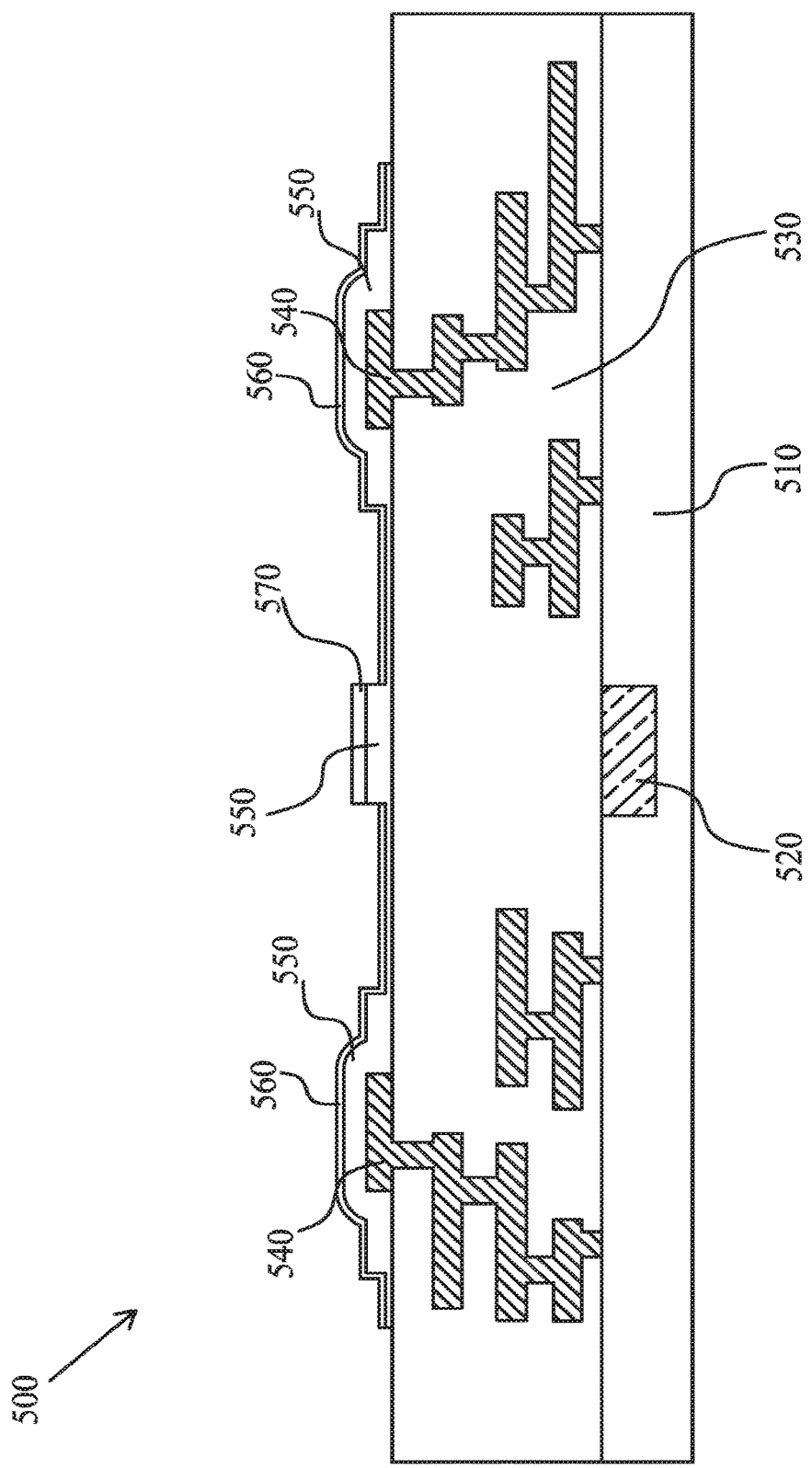
FIG. 5 is a cross-sectional diagram of a lower wafer for use in a bio-entity manipulation and processing system according to an embodiment.

FIG. 5 is a cross-sectional diagram of a lower wafer 500 having a lower substrate 510 for use in a microfluidic bio-entity manipulation and processing system. The lower substrate 510 includes a fluidic control circuitry area, a solid-state based photosensor area, a logic circuitry area, and a microfluidic channel area. The circuitry and photosensor areas are formed on or in the lower substrate 510. As depicted, lower substrate 510 is a silicon substrate. However, in other embodiments, lower substrate 510 may be a substrate formed from another suitable elementary semiconductor, such as diamond or germanium; a suitable compound semiconductor, such as silicon carbide, indium arsenide, or indium phosphide; or a suitable alloy semiconductor, such as silicon germanium carbide, gallium arsenic phosphide, or gallium indium phosphide.

The fluidic control circuitry area includes fluidic control circuitry, which includes a plurality of metallization layers connected with associated transistors and other circuit components. The sensor area includes a photosensor array 520 and photosensor control circuitry. In the depicted embodiment, the photosensor array 520 is an array of transistor-based photosensors and is a CMOS image sensor array. However, in other embodiments the photosensor array 520 may include photodiodes, active pixel sensors, phototransistors, photoresistors, charged coupled devices, or the like. The photosensor array 520 is controlled by the photosensor control circuitry, which also includes a plurality of transistors and other circuit components. Finally, in the logic circuitry area, there is a significant amount of logic circuitry, including transistors and other circuit components. The logic circuitry allows for input to and output from the lower substrate 510. Further logic circuitry is coupled to both the photosensor control circuitry and the fluidic control circuitry, to provide both with signal processing for optimal operation, such as analog-to-digital and digital-to-analog conversion. Fluidic control circuitry, photosensor control circuitry, and logic circuitry are embedded in an inter-level dielectric layer (ILD) 530.

On top of the ILD 530, is a plurality of bottom electrodes, much like the bottom electrodes of FIG. 2. In FIG. 5, two bottom electrodes 540 are depicted. Many more electrodes may be present in practice, but the two depicted are adequate for clear discussion of lower substrate 510. In the depicted embodiment, bottom electrodes 540 are made from an aluminum-copper alloy. However, in other embodiments different materials may be used that are also suitable for electrodes. Bottom electrodes 540 are solid rectangles as viewed from above. The bottom electrodes 540 are in communication with the fluidic control circuitry, and thus all may be in an ON or OFF state as described in connection with FIG. 3.

On top of and surrounding the sides of bottom electrodes 540 is a dielectric layer 550. In the depicted embodiment, dielectric layer 550 is a high-k dielectric layer formed by an atomic layer deposition (ALD) process, or a chemical vapor deposition (CVD) process, then followed by an annealing process. Over the dielectric layer 550 is a hydrophobic coating 560. In the depicted embodiment, hydrophobic coating 560 is made from polytetrafluoroethylene (PTFE), while in other embodiments it is a self-assembled monolayer.

A portion of the dielectric layer 550 has been treated with a surface treatment to create a surface treated area 570. In the depicted embodiment, the surface treated area 570 may contain receptors to promote DNA sequencing, while in other embodiments, a surface treatment with antibody binding receptors may be applied. The surface treated area 570 allows identifiable reactions to take place that give of light when a droplet containing components that react with the particular receptors are brought into contact with the surface treated area 570. For example, a molecular tag may be added onto base pairs that combine with the target DNA fragment, releasing the tag upon combination, with the release of the tag emitting a light signal.

Figure 6:
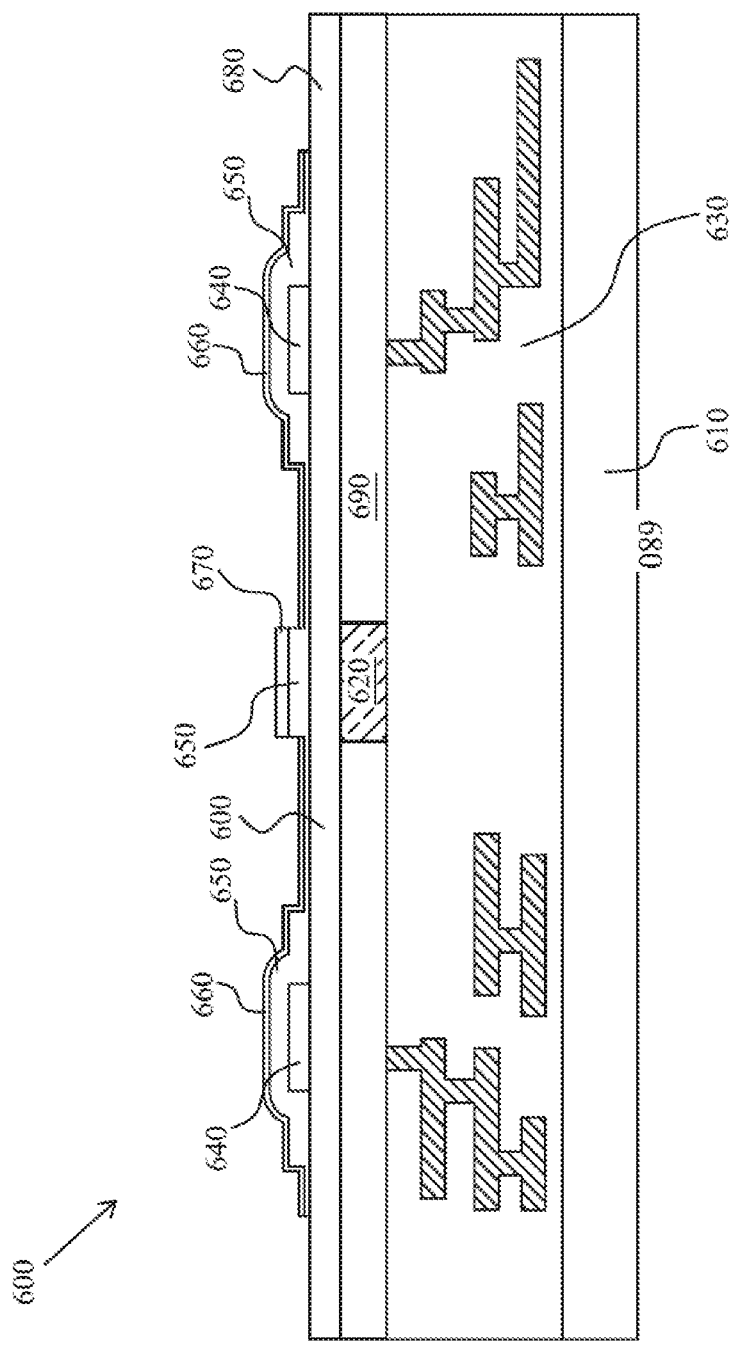
FIG. 6 is a cross-sectional diagram of a lower wafer for use in a bio-entity manipulation and processing system according to another embodiment.

FIG. 6 illustrates another embodiment of a lower wafer 600, that allows the photosensor array 620 to be closer to the surface treated area 670. In between photosensor array 620 and the surface treated area 670 is an oxide or anti-reflecting coating (ARC) layer 680. The photosensor array 620 is on another substrate 690, which may be silicon. Like the lower wafer 500, the lower wafer 600 also includes ILD 630, bottom electrodes 640, dielectric layer 650, and hydrophobic coating 660.

Figure 7:
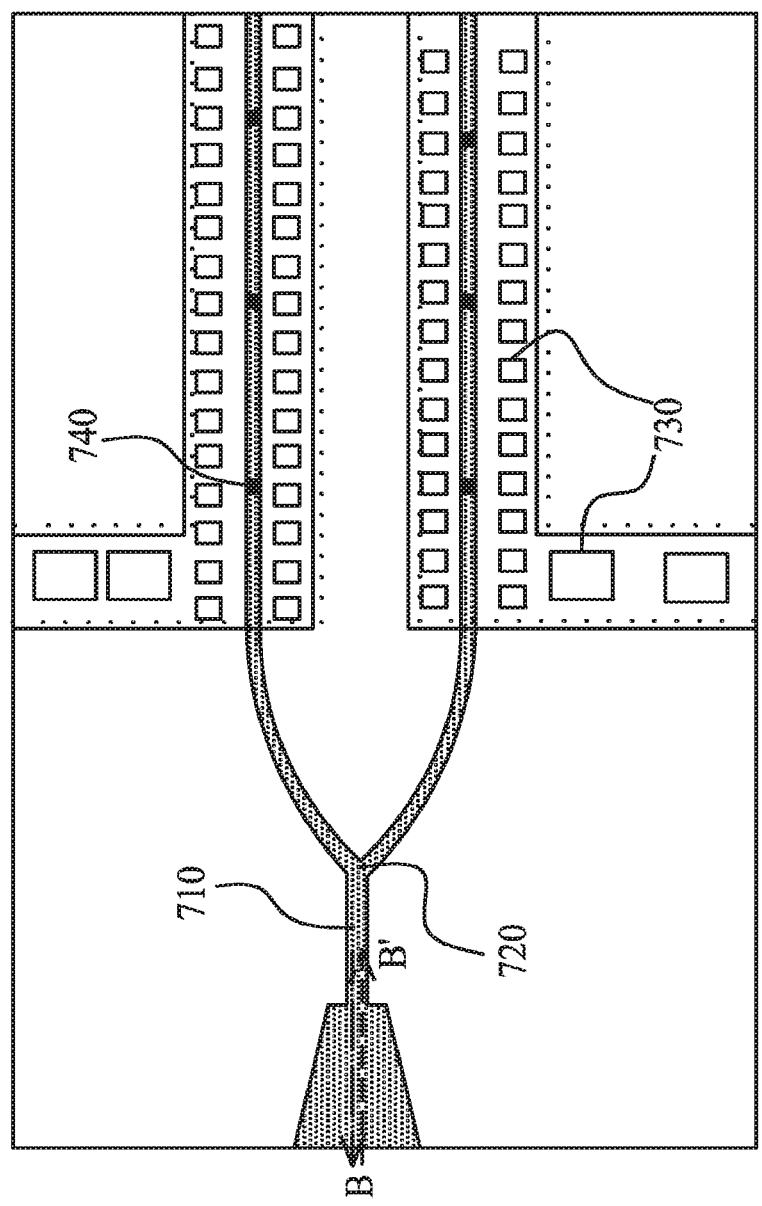
FIG. 7 is a top view diagram of a lower wafer for use in a bio-entity manipulation and processing system according to an embodiment.

FIG. 7 illustrates a top view of the upper wafer 500 or 600. The dielectric layer 550 and 650 is formed on the lower substrate 510 and 610 and functions as an optical signal conduit or waveguide 710 with input structures configured to couple an input source to the optical signal conduit 710. Attached to the optical signal conduit 710 is a waveguide splitter 720 for splitting the optical signal conduit 710 into different pathways. Although the waveguide splitter 720 is shown splitting the optical signal conduit 710 into two pathways, it should be understood that more than two pathways may be formed by the waveguide splitter 720. Also shown are electrodes 730 covered in the dielectric layer 550 or 660 and hydrophobic coating 560 and 660, and surface treated area 740. Many other suitable electrode configurations may be used besides the one shown.

Figure 8A:
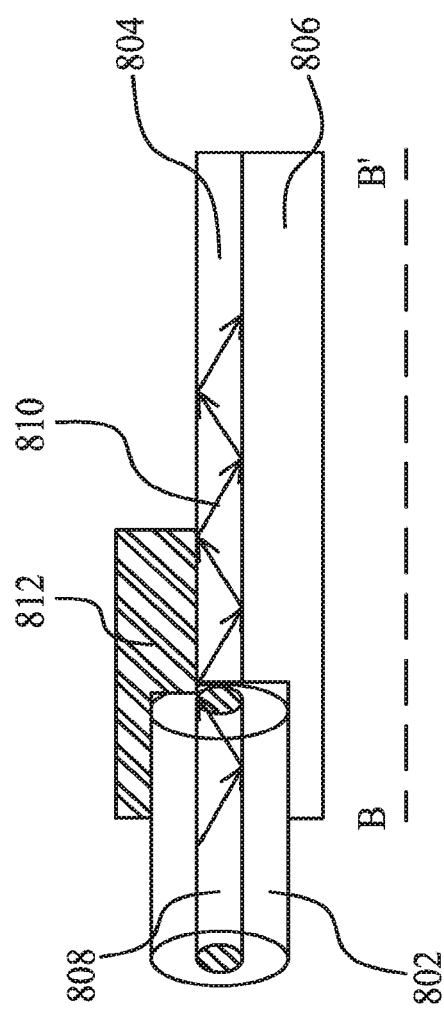
FIGS. 8A and 8B are side view diagrams illustrating optical conduits and optical inputs on a lower wafer for use in a bio-entity manipulation and processing system according to an embodiment.
Figure 8B:
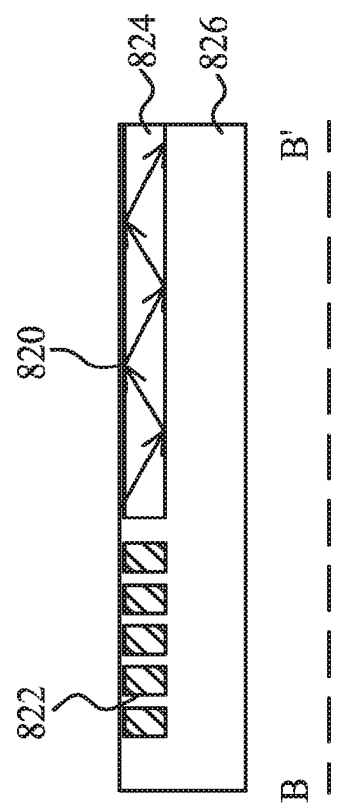

FIGS. 8A and 8B show the optical signal conduit along the line B-B' in FIG. 7. FIG. 8A illustrates an optical cable 802 input. The optical signal conduit 804 is formed on the substrate 806. The optical cable 802 may be attached to the substrate 806 so that an optical core 808 of the optical cable 802 provides an optical path for incoming light 810 to the optical signal conduit 804. The optical cable 802 may be attached and held in place by an adhesive 812 such as polydimethylsiloxane (PDMS), by an adhesive fastening system, or by any other suitable attachment system FIG. 8B is a side view diagram illustrating an alternative embodiment. The optical signal conduit 824 is formed on the substrate 826. The optical signal conduit 824 has a grating coupler 822. In such an embodiment, a laser or other light source may be provided remotely, and may be directed into the grating coupler 822 where incoming light 820 it is transmitted into the optical conduit 824.

Figure 9E:
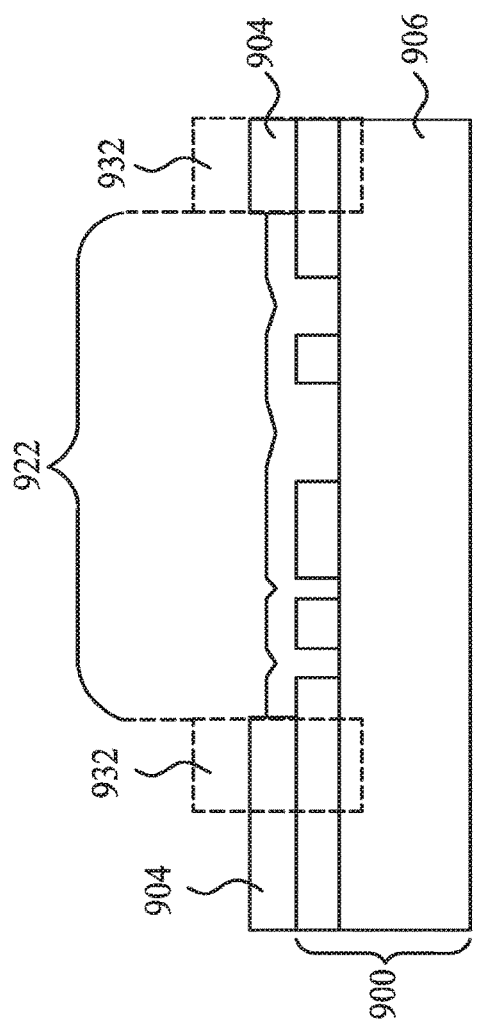

FIGS. 9A-9F are cross sectional views of a lower wafer 900 at various stages of manufacture according to one or more embodiments. Initially, FIG. 9A illustrates a lower wafer 900 in an early stage of manufacture. An optical signal conduit 902 may be disposed on a substrate 906, with the substrate 906 being a material such as, but not limited to, glass, silicon (Si), gallium arsenide (GaAs), fiberglass, metal, or the like. Additionally, the substrate 906 may contain circuitry such as CMOS devices; interconnect lines; sensors; electrodes; photodetectors; doped regions, or the like, such as photosensor arrays 520, 620; ILD 530, 630; and bottom electrodes 540, 640. In one embodiment, the optical signal conduit 902 may be patterned to disperse light, or to provide separate conduit sections. An optical signal conduit 902 may, for example, be a dielectric material such as silicon nitride (Si3N4), silicon oxynitride (SiON), hafnium dioxide (HfO2), tantalum pentoxide (Ta2O5), or the like. A typical optical signal conduit 902 thickness may be between about 500 angstroms and about 6000 angstroms. In one embodiment, a dry etching technique may be employed to pattern the optical signal conduit 902, and may provide better optical conduit critical dimension control than wet etching. Additionally, some embodiments may have an optical signal conduit 902 with a smooth outer surface, resulting in more efficient transmission of an optical signal.

FIG. 9B illustrates a cross-sectional view of a lower wafer 900 after forming a sacrificial layer 912. In one embodiment, a sacrificial layer 912 may be a hard or non-polymer material such as germanium (Ge), silicon (Si), titanium tungsten alloy (TiW), aluminum (Al), or the like, and may advantageously be deposited over the substrate 906 and optical signal conduit 902 by plasma deposition, chemical vapor deposition, physical vapor deposition, or the like. In one embodiment, the sacrificial layer 912 may have a thickness between about 2000 angstroms and about 6000 angstroms.

FIG. 9C illustrates a cross-sectional view of a lower wafer 900 after patterning the sacrificial layer 912. The sacrificial layer 912 may be patterned or removed from regions outside of the future packaging covered area 922 via lithography, or any other suitable process, leaving sacrificial layer 912 material only in the packaging covered area 922. Removal of the sacrificial layer 912 may be accomplished by an etchant appropriate for the particular sacrificial layer 912 material, including, but not limited to, hydrogen peroxide (H2O2), phosphoric acid (H3PO4), potassium hydroxide (KOH), tetramethylammonium hydroxide (TMAH), ethylenediamine pyrocatechol (EDP), xenon diflouride (XeF2), and the like.

FIG. 9D illustrates a cross sectional view of a lower wafer 900 after forming a bonding layer. A bonding layer 934 may be deposited over the patterned sacrificial layer 912 and optical signal conduit 902. In one embodiment, the bonding layer 934 may be applied so that it lies in the bonding area 932 to cover the optical signal conduit 902 and provide a pad for bonding a cap wall over the signal conduit 902. The bonding layer 934 may be, in some embodiments, an oxide such as silicon dioxide or the like, and may be deposited via, for example, a chemical vapor deposition process, a plasma enhanced deposition process, or any other suitable process. Alternatively, the bonding layer 934 may be a nitride, a metal layer, a polysilicon layer, or the like, and the bonding layer material may be selected depending on the optical signal conduit 902 properties. The sacrificial layer 912 may shield the optical signal conduit 902 from an overlying bonding layer 934, in the region where the bonding layer 934 will later be removed.

In one embodiment of the present principles, it may be advantageous to have a hard sacrificial layer 912 instead of a sacrificial photoresist (PR) under the bonding layer 934 because polymer residues could interfere with the surface chemistry of the lower wafer 900. Additionally, the planarization of bonding layer 934 that would be deposited on a sacrificial photoresist layer may be problematic because the oxide is on a soft material: the stress and pressure from planarization may cause a polymer-type photoresist to deform and the bonding layer to fail during the planarization. However, a biocompatible photoresist may be used, and the chemistry of such a biocompatible photoresist may be determined by the test material intended for a capped area, which will be discussed later. In such an instance, a biocompatible photoresist chemistry will preferably be selected to not interfere with the testing procedure and chemistry of any target molecule.

The bonding layer 934 may be deposited at a thickness over the substrate 906 surface between about 4 micrometers (40,000 angstroms) and 0.5 micrometers (5,000 angstroms) and may be subsequently planarized, using for example, a chemical mechanical polish, down to a thickness between about 2 micrometers (20,000 angstroms) and about 0.4 micrometers (4,000 angstroms). The bonding layer 934 may provide a planarized surface capable of accepting a range of bonding technologies while permitting an optical signal conduit 902 thickness up to about 600 nanometers (6,000 angstroms). Thus, one useful embodiment may be where the optical signal conduit is between about 200 nanometers (2,000 angstroms) and about 600 nanometers (6,000 angstroms) thick, and the bonding layer covers the optical signal conduit 902 while having a planarized bonding surface.

FIG. 9E illustrates a cross sectional view of a lower wafer 900 after patterning the bonding layer 934. The bonding layer 934 may be patterned or formed into cap bonding pads 904 by etching to remove the bonding layer 934 material in order to define or form a packaging covered area 922, with bonding layer 934 material remaining in the bonding areas 932 as a target for bonding cap walls 904. In one particularly useful embodiment, the bonding layer 934 may be etched using a dry etch technique, such as plasma etching or ionic sputtering. Alternatively, and depending on the bonding layer 934 material, a wet etch, or any other type of etching, may be advantageously employed to pattern the bonding layer 934. In one embodiment, the bonding layer 934 may be planarized prior to patterning, which may avoid damage or contamination of portions of the substrate or optical signal conduit that may be unintentionally exposed from topography-induced insufficient mask or photoresist coverage during patterning. Additionally, planarizing the bonding layer 934 prior to patterning reduces or prevents damage or destruction by planarization of regions whose bonding layer has been patterned away.

Figure 9F:
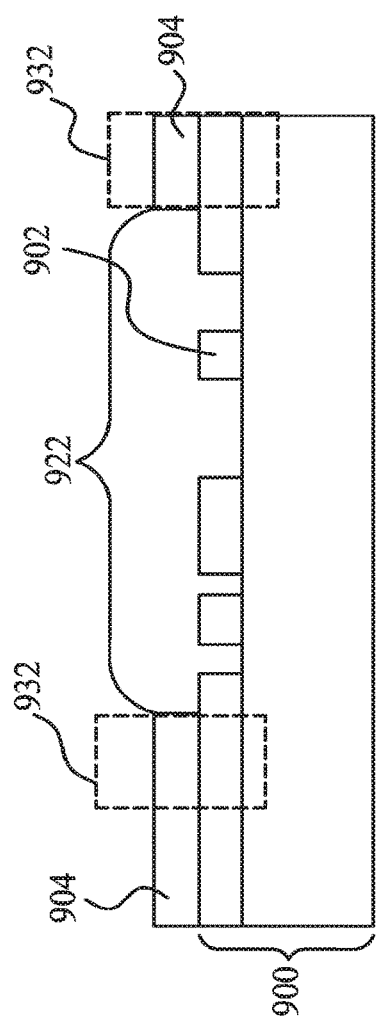

FIG. 9F illustrates a cross-sectional view of a lower wafer 900 after the sacrificial layer 912 is removed, exposing the optical signal conduit 902. Removal of the sacrificial layer 912 may be performed by, for example, a wet or vapor etch in a similar manner as described above for the sacrificial layer 912 patterning. Thus, the optical signal conduit 902 is exposed in the packaging covered area 922.

Figure 10:
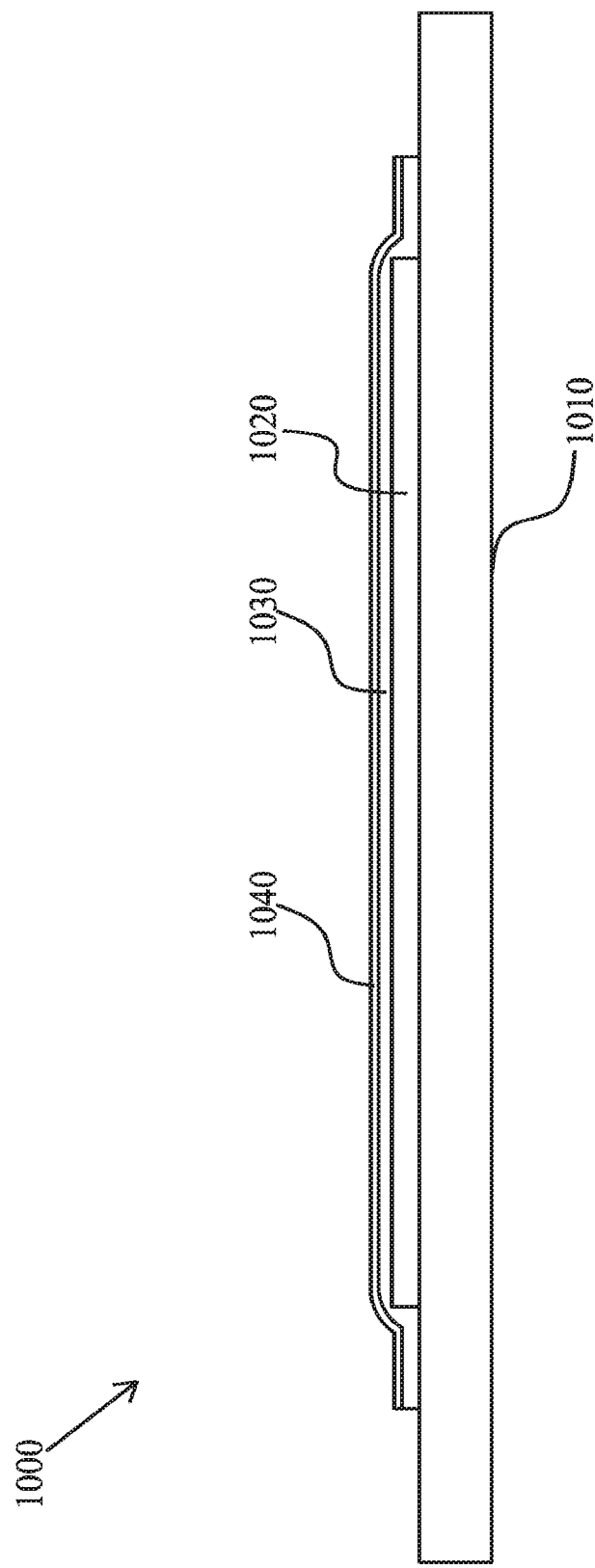
FIG. 10 is a cross-sectional diagram of an upper wafer that may be used in a bio-entity manipulation and processing system according to an embodiment.

FIG. 10 is a cross-sectional diagram of an upper wafer 1000 that may be used in a bio-entity manipulation and processing system. The upper wafer 1000 includes an upper substrate 1010. In the depicted embodiment, an upper substrate 1010 is a glass or silicon wafer, and does not need to be transparent. However, in other embodiments, upper substrate 1010 may be a substrate formed from another suitable elementary semiconductor, such as diamond or germanium; a suitable compound semiconductor, such as silicon carbide, indium arsenide, or indium phosphide; or a suitable alloy semiconductor, such as silicon germanium carbide, gallium arsenic phosphide, or gallium indium phosphide. Over upper substrate 1010 is a top electrode 1020. In the depicted embodiment, top electrode 1020 is an indium tin oxide (ITO) layer. However, in other embodiments, top electrode 1020 may be an aluminum layer, aluminum-copper alloy layer, or another suitable electrode layer.

A dielectric layer 1030 is deposited over the top electrode 1020. In this example, the dielectric layer 1020 is a high-k dielectric layer that has been deposited by an ALD process before being annealed. Additionally, on top of the dielectric layer 1030 is a hydrophobic coating 1040. In the depicted embodiment, the hydrophobic coating 1040 is made from PTFE, but in other embodiments the hydrophobic coating 1040 is made from a self-assembling monolayer.

Figure 11A:
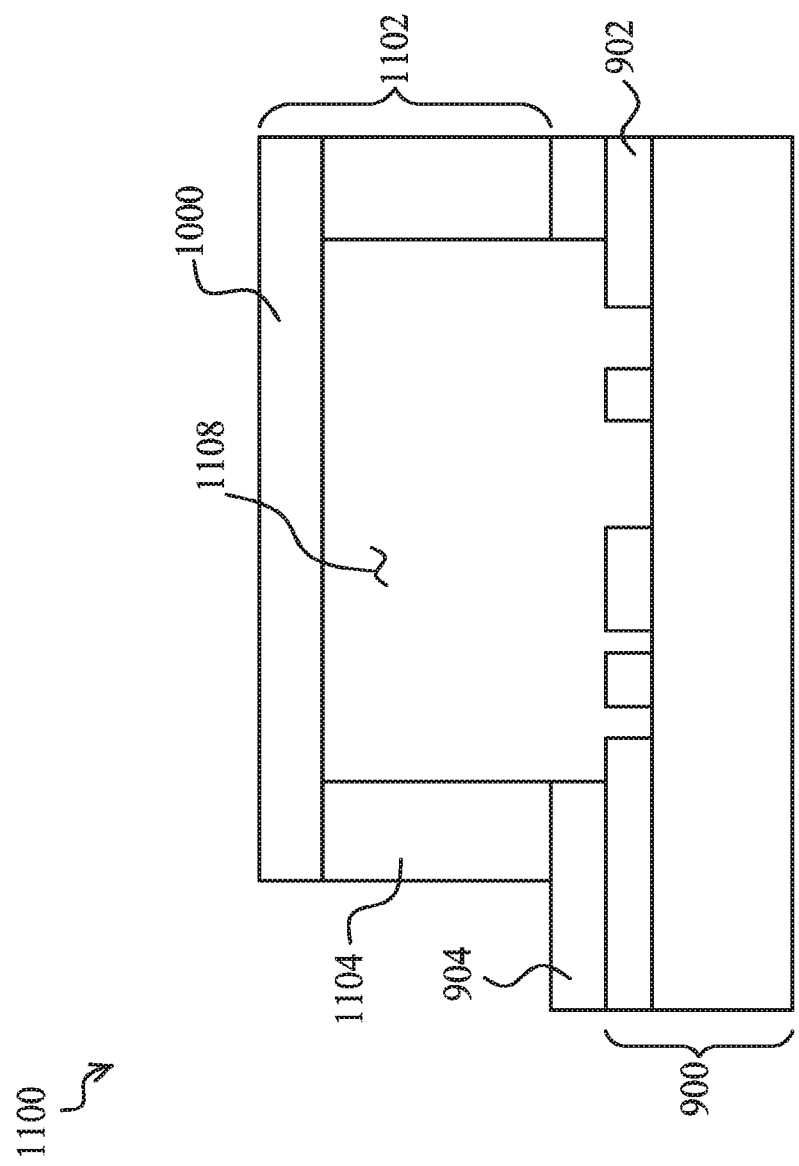

FIGS. 11A and 11B illustrate a bonding of a lower wafer 900 and an upper wafer 1000 for use in a bio-entity manipulation and processing system 1100. FIG. 11A illustrates an embodiment of a bio-entity manipulation and processing system 1100 with cap bond pads 904 disposed under the cap wall 1104 and covering the optical signal conduit 902 outside of the capped area 1108. FIG. 11B illustrates an embodiment of a bio-entity manipulation and processing system 1100 with cap bond pads 904 disposed in the area under the cap wall 1104 but exposing the exterior portions of the optical signal conduit 902. The cap bond pad 904 and sacrificial material 912 remaining outside the capped area 1108 may be removed to expose the exterior portion of the optical signal conduit 902 during the steps illustrated in FIGS. 9B through 9F. Alternatively, the exterior portion of the optical signal conduit 902 may be exposed in a separate step, for example, after the cap 1102 is applied to the cap bond pads 904.

The cap wall 1104 may be bonded to the cap bonding pads 904 using an adhesive such as an epoxy, via fusion bonding, or any other suitable technique. In one useful embodiment, for example, fusion bonding with low temperature (<300° C.) anneal may be suitable where the cap bonding pad 904 material is an oxide. The upper wafer 1000 may be bonded to the cap wall 1104 to form a cap 1102 and define the capped area 1108. The capped area 1108 may be provided with a gaseous environment or fluidic material prior to bonding the upper wafer 1000, or via a sealable opening after the cap 1102 is bonded. The cap 1102 will preferably be configured to remain water- or liquid-tight in an embodiment where the capped area maintains a fluidic material Likewise where the capped area 1108 maintains a gaseous material, the cap 1102, including the cap's structures and bonded seams will be gas-impermeable.

Separation of the bonding material and cap walls 1104 from the optical signal conduit 902 by the cap bonding pads 904 permits a planar bonding surface, since the bonding layer 934 and cap bonding pads 904 are laid over the signal conduit 902 and substrate 906 and then planarized. As the bonding pad 904 is planarized, the bonding pad 904 may be used to compensate for topography created by the optical signal conduit 902 as well as by the substrate 906. Skilled artisans will recognize that in order to maintain a suitable planar surface, the cap bonding pads 904 will be at least as thick as the optical signal conduit 902 is high so that the cap bonding pads 904 lie on top of the optical signal conduit 902. In particularly useful embodiments, the optical signal conduit 902 will be less than about 600 nanometers, with the planarized cap bonding pads 904 being thicker than the optical signal conduit 902.

Figure 12:
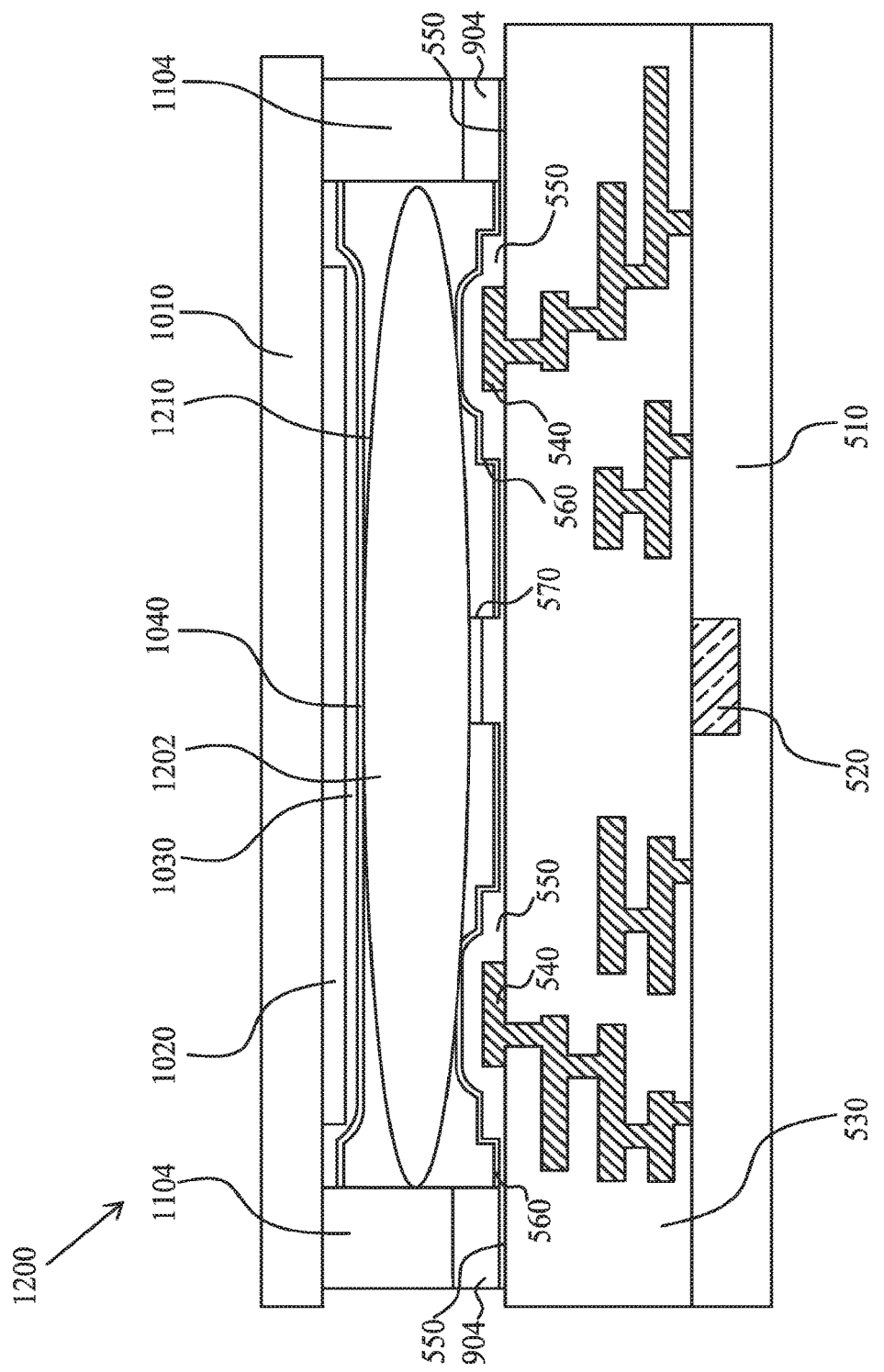
FIG. 12 is a cross-sectional diagram of a microfluidic bio-entity manipulation and processing system according to an embodiment.

FIG. 12 is a cross-sectional diagram of an integrated microfluidic bio-entity manipulation and processing system 1200 that integrates the lower wafer 500 of FIG. 5 and the upper wafer 1000 of FIG. 10. Thus FIG. 12 includes the substrate 510, with the fluidic control circuitry, the photosensor control circuitry, and the logic circuitry thereon, in addition to the photosensor array 520 therein. An ILD 530 surrounds those features, and the integrated lower wafer 500 includes bottom electrodes 540 deposited thereon with an overlying dielectric layer 550. In certain regions where the dielectric layer 550 does not cover the electrodes, the dielectric layer 550 can function as an optical signal conduit, as described with respect to FIGS. 7 through 9F. On top of the dielectric layer 550 is a hydrophobic coating 560 that serves as the bottom of a microfluidic channel 1210.

The microfluidic bio-entity manipulation and processing system 1200 also includes upper wafer 1000, which includes upper substrate 1010, which in this embodiment is a silicon substrate. Over upper substrate 1010 are a top electrode 1020, a dielectric layer 1030, and a hydrophobic coating 1040. The lower wafer 500 and upper wafer 1000 are combined using the methods described with respect to FIGS. 11A and 11B so that the surface treated area 570 is aligned with the photosensor array 520 and so that the hydrophobic coatings 560 and 1040 are brought close together, without contacting, to form the microfluidic channel 1210. In the depicted embodiment the surface treated area 570 is formed on hydrophobic coating 560, which may improve performance by bringing the surface treated area 570 closer to photosensor array 520. The presence of hydrophobic coating 560 below surface treated area 570, however, is not required.

In operation, a droplet 1202 is brought into contact with the surface treated area 570 containing receptors using the actions depicted in FIG. 3, such as the lateral movement 300A. The droplet 1202 includes a tagged bio-entity sample, such as a specific DNA base mixed in the droplet such as the exemplary adenine reagent droplet 408B from FIG. 4. When the droplet 1202 contacts the receptors at the surface treated area 570, chemical reactions may remove the tag from the bio-entity samples in the droplet. The removal of the tag may enhance or intensify a photonic emission. In some embodiments, the attachment rather than the removal of the tag may enhance or intensify a photonic emission. The emission is sensed in the photosensor array 520. This signal is captured by the photosensor control circuitry, and transmitted to the logic circuitry for signal processing. Depending on the frequency or color of the photonic emission, a specific base pair may be detected. In embodiments, in which antibodies in the droplet 1202 are being tested, the emission may indicate the presence of the particular antibody in the bio-entity sample in droplet 1202. After the droplet 1202 has been processed in this manner, it may be moved out of the microfluidic channel 1210, and may be moved out of the microfluidic grid 400.

Figure 13:
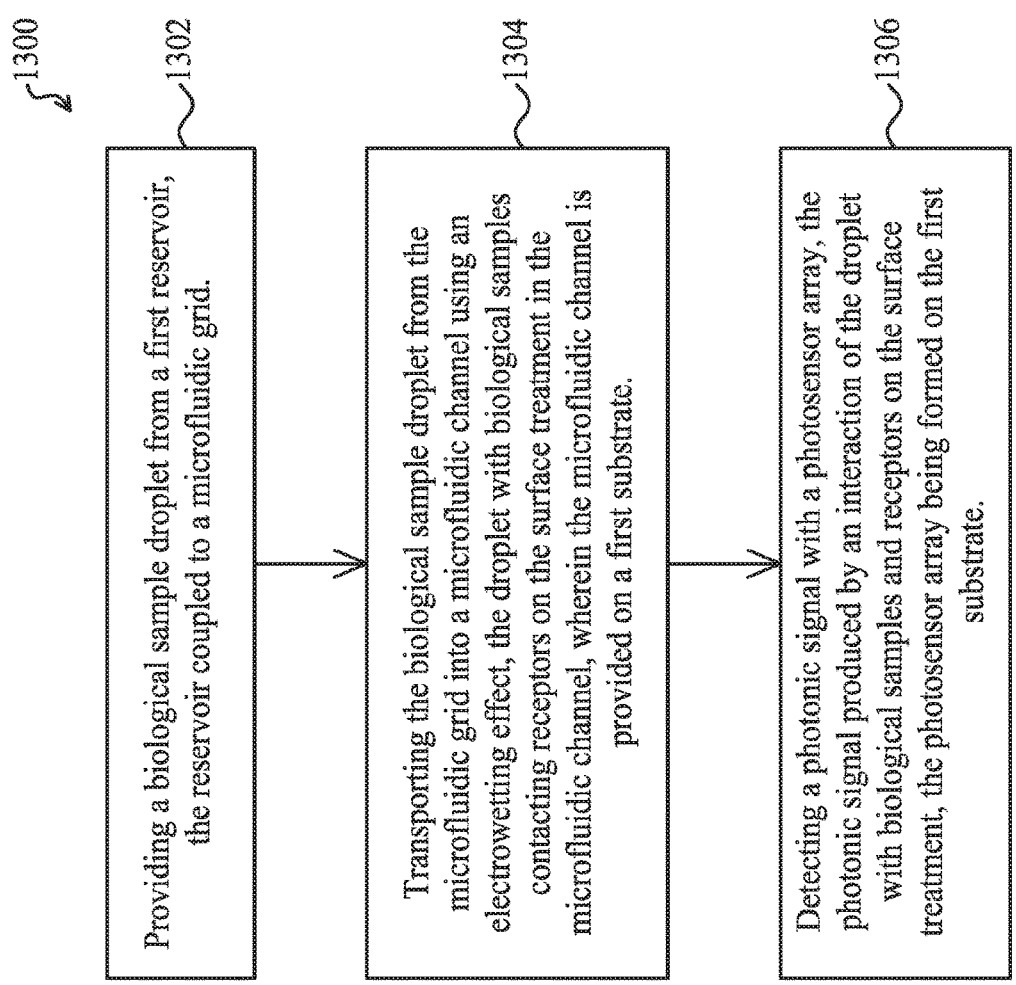
FIG. 13 is a flowchart of a method for manipulating and processing bio-entity samples with an integrated semiconductor device.

A method 1300 for manipulating and processing bio-entity samples with an integrated semiconductor device will now be described with respect to FIG. 13. The method begins at step 1302 when a bio-entity sample droplet is obtained from a first reservoir. The first reservoir is coupled to a microfluidic grid. The method 1300 continues to step 1304 when the bio-entity sample droplet is transported from the microfluidic grid into a microfluidic channel using an electrowetting effect. In the microfluidic channel, the bio-entity sample droplet contacts the receptors on the surface treatment in the microfluidic channel. A biochemical reaction is triggered upon contact between the bio-entity sample droplet and the receptors on the surface treatment. At step 1306, a photonic signal that is produced by the interaction of the bio-entity sample droplet and the receptors on the surface treatment is detected by a photosensor array that is formed on the lower or first substrate.

To better illustrate the method 1300 in operation, reference will be made to the integrated microfluidic bio-entity manipulation and processing system 1200 of FIG. 12 and some other figures discussed above such as FIG. 3 and FIG. 4. The method may also be explained with reference to other embodiments of integrated microfluidic bio-entity manipulation and processing systems disclosed herein. Thus, reference to FIG. 12 is made by way of non-limiting example. A reservoir 410A of FIG. 4 may include a larger volume of a bio-entity sample. By using the action depicted as droplet formation 300D of FIG. 3, a bio-entity sample droplet 1202 is formed from the larger volume and introduced into the microfluidic grid 400 of FIG. 4. The bio-entity sample droplet 1202 is transported through microfluidic grid 400, which includes a plurality of microfluidic channels, one of which is microfluidic channel 1210 of FIG. 12. Microfluidic channel 1210 is located on top of a material stack deposited on lower substrate 510, the top layer of which, hydrophobic coating 560, supplies the bottom surface of the microfluidic channel 1210. Transporting the bio-entity sample droplet 1202 through the microfluidic channel 1210 is accomplished by using the logic circuitry to control the fluidic control circuitry.

The bio-entity sample droplet 1202 is moved through the microfluidic grid 400 of FIG. 4 and the microfluidic channel 1210 of FIG. 12 by using the electrowetting effect. Bottom electrodes 540 are asserted in either ON or OFF states as indicated by FIG. 3, in order to subject the biological droplet 1202 to controlled hydrophobic or hydrophilic surfaces according to the ON or OFF states of the bottom electrodes. By control of the bottom electrodes 540, and in conjunction with a top electrode 1020, the bio-entity sample droplet 1202 is guided into contact with the surface treated area 570, which has had a surface treatment applied to it. Guiding the bio-entity sample droplet 1202 into contact with the surface treated area 570 is accomplished by having the logic circuitry exert control over the fluidic control circuitry.

Because of the surface treatment, receptors in the surface treated area 570 and the bio-entity sample droplet 1202 may undergo a biochemical reaction which intensifies or enhances the fluorescent light signal. This light is received by a photosensor array 520. Photosensor 520 detects the light and a corresponding signal is sent to the logic circuitry for processing. The logic circuitry may interpret the signal by color or frequency to determine the biochemical reaction that occurred. The biochemical reaction may indicate that a specific base nucleotide was detected in a target DNA fragment, or that a particular antibody was present in the bio-entity sample droplet. After the bio-entity sample droplet 1202 has been processed, it may be removed from the microfluidic channel 1210. In some embodiments a buffer droplet, such as buffer droplet 408A of FIG. 4, may be transported through the microfluidic channel 1210 in order to clean it.

Additionally, in some embodiments of the method, an adenine reagent droplet 408 B obtained from the adenine reagent tank 406A in FIG. 4 is combined with the bio-entity sample droplet 1202, using the droplet merge 300C operation of FIG. 3. The droplet merge 300C operation may mix the bio-entity sample droplet 1202 and the adenine reagent droplet 408B in the microfluidic grid 400. The mixed bio-entity sample droplet 1202 may then be directed into contact with the surface treated area 570 in the microfluidic channel 1210. In other embodiments, a reagent other than the adenine reagent droplet 408B may be used to create a different mixed bio-entity sample droplet 1202.

Advantages of the integrated microfluidic bio-entity manipulation and processing system are provided by the optical signal conduit on the substrate 510. Light delivery to the analysis site via the evanescent wave is done through the optical signal conduit, thus making the need for a transparent substrate and transparent top electrode unnecessary for a bio-entity analysis scheme involving EWOD. This provides for greater flexibility in the materials used. Moreover, bio-entity analysis involving the optical signal conduit may avoid the need for color filters integrated above the photosensors because the EWOD method can restrict particular base pairs to be sequenced at the moment, avoiding the need for color differentiation. One of the broader embodiments is an integrated semiconductor device for manipulating and processing bio-entity samples. The device includes a lower substrate, at least one optical signal conduit disposed on the lower substrate, at least one cap bonding pad disposed on the lower substrate and over a portion of the optical signal conduit, a cap that includes an upper substrate and configured to form a capped area, and disposed on the at least one cap bonding pad, a microfluidic channel, a photosensor array coupled to sensor control circuitry, and logic circuitry coupled to the fluidic control circuitry and the sensor control circuitry. The at least one optical signal conduit extends from outside the capped area to inside the capped area. The first side of the microfluidic channel is formed on the lower substrate and a second side of the microfluidic channel is formed on the cap, the cap being coupled to the substrate so as to provide the microfluidic channel for a droplet containing a bio-entity sample and the microfluidic channel being coupled to fluidic control circuitry. The fluidic control circuitry, the sensor control circuitry, and the logic circuitry are formed on the lower substrate.

Another of the broader embodiments is an integrated semiconductor device for manipulating and processing genetic samples. The device includes a lower substrate, at least one optical signal conduit disposed on the lower substrate and configured to transmit light to a target molecule, at least one cap bonding pad disposed on the lower substrate and over a portion of the optical signal conduit, a cap comprising an upper substrate and configured to form a capped area, and disposed on the at least one cap bonding pad, a surface treated area with receptors disposed within the capped area and on the lower substrate and configured to interact with the target molecule, a microfluidic channel, and a photodetector disposed within the lower substrate and configured to detect a response from the target molecule. The at least one optical signal conduit extends from outside the capped area to inside the capped area. A bottom surface of the microfluidic channel is formed on the lower substrate and a top surface of the microfluidic channel is formed on the cap, the cap being coupled to the substrate so as to provide the microfluidic channel.

Yet another of the broader embodiments is a method for manipulating and processing bio-entity samples with an integrated semiconductor device. The method includes providing a bio-entity sample droplet from a first reservoir, the first reservoir coupled to a microfluidic grid, transporting the bio-entity sample droplet from the microfluidic grid into a microfluidic channel using an electrowetting effect, the bio-entity sample droplet contacting a surface treatment in the microfluidic channel, wherein one side of the microfluidic channel is provided on a lower substrate, transmitting light to the surface treatment through an optical signal conduit disposed on the lower substrate, and detecting a photonic signal with a photosensor array, the photonic signal being enhanced by an interaction of the bio-entity sample droplet and the surface treatment, the photosensor array being formed on the lower substrate.

The preceding disclosure is submitted by way of discussion and example. It does not exhaust the full scope and spirit of the disclosure and claims. Such variations and combinations as may be apparent to one of skill in the art are considered to be within the scope and spirit of this disclosure. For instance, throughout the disclosure, DNA sequencing is presented as an example, along with antibody identification. The scope and spirit of the disclosure extends well beyond the limited context of these examples. Thus, the full extent of the disclosure is limited only by the following claims.

What is claimed is:

1. An integrated circuit device comprising:
    a substrate;
    at least one optical signal conduit disposed on the substrate;
    a cap configured to form a capped area, wherein the at least one optical signal conduit extends from outside the capped area to inside the capped area; and
    a fluidic channel, wherein a first side of the fluidic channel is formed on the substrate and a second side of the fluidic channel is formed on the cap, the cap being coupled to the substrate and the fluidic channel being coupled to fluidic control circuitry.

2. The device of claim 1 further comprising:
    a photosensor array coupled to sensor control circuitry; and
    logic circuitry coupled to the fluidic control circuitry and the sensor control circuitry, wherein the fluidic control circuitry, the sensor control circuitry, and the logic circuitry are formed on the substrate.

3. The integrated semiconductor device of claim 2, wherein the fluidic control circuitry, the sensor control circuitry, and the logic circuitry are embedded in an inter-level dielectric (ILD) layer, and further comprise a plurality of electrodes over the ILD layer, the plurality of electrodes being coupled to the fluidic control circuitry.

4. The integrated semiconductor device of claim 1, wherein the first side of the fluidic channel comprises:
    a high-k dielectric layer; and
    a hydrophobic coating covering the high-k dielectric layer.

5. The integrated semiconductor device of claim 1, wherein the second side of the fluidic channel comprises:
    a dielectric layer over the cap; and
    a hydrophobic coating over the dielectric layer.

6. The integrated semiconductor device of claim 1, further comprising a surface treated area, the surface treated area disposed on the high-k dielectric layer of the first side of the fluidic channel.

7. The integrated semiconductor device of claim 1, wherein the fluidic channel is coupled to a fluidic grid, the fluidic grid being coupled to a plurality of reservoirs and configured to allow for transport and mixing of fluids contained in the plurality of reservoirs, the fluids including bio-entity samples and reagents.

8. The integrated semiconductor device of claim 1, wherein the optical signal conduit is configured to transmit light to a target molecule and wherein a photodetector is configured to detect a response from the target molecule.

9. The integrated semiconductor device of claim 1, wherein the cap is not transparent.

10. The integrated semiconductor device of claim 1, further comprising a plurality of electrodes over the cap and under a high-k dielectric layer, wherein the electrodes are not transparent.

11. An integrated semiconductor device comprising:
    a substrate;
    at least one optical signal conduit disposed on the substrate and configured to transmit light to a target molecule;
    a capped area above the substrate, wherein the at least one optical signal conduit extends from outside the capped area to inside the capped area;
    a surface treated area with receptors disposed within the capped area and on the substrate and configured to interact with a target molecule;
    a fluidic channel, wherein a bottom surface of the fluidic channel is formed on the substrate and a top surface of the fluidic channel is formed at the capped area; and
    a photodetector disposed within the substrate and configured to detect a response from the target molecule.

12. The integrated semiconductor device of claim 11, further comprising a cap bonding pad and a cap, the cap including an upper substrate and configured to form the capped area.

13. The integrated semiconductor device of claim 11, wherein the bottom surface and the top surface of the fluidic channel comprise a hydrophobic coating.

14. The integrated semiconductor device of claim 13, wherein the bottom surface and the top surface of the fluidic channel further comprise a high-K dielectric layer.

15. The integrated semiconductor device of claim 11, wherein an oxide or anti-reflective coating is disposed between the photodetector and the surface treated area.

16. The integrated semiconductor device of claim 11, further comprising a plurality of electrodes disposed on the substrate.

17. A method for manipulating and processing samples with an integrated semiconductor device, the method comprising:
providing a sample from a first reservoir, the first reservoir coupled to a fluidic grid;
transporting the sample from the fluidic grid into a fluidic channel, the sample contacting a surface treatment in the fluidic channel, wherein one side of the fluidic channel is provided on a substrate;
transmitting light to the surface treatment through an optical signal conduit disposed on the substrate; and
detecting a photonic signal, the photonic signal being enhanced by an interaction of the sample and the surface treatment.

18. The method of claim 17, further comprising:
providing a reagent from a second reservoir coupled to the fluidic grid; and
mixing the sample and the reagent in the fluidic grid to form a prepared sample droplet.

19. The method of claim 18, wherein transporting the sample from the fluidic grid into a fluidic channel comprises transporting the prepared sample droplet into the fluidic channel.

20. The method of claim 17, further comprising providing an optical cable input that provides an optical path for light to the optical signal conduit or providing a grating coupler.

* * * * *